US011842406B2

(12) United States Patent
Magnuson et al.

(10) Patent No.: US 11,842,406 B2
(45) Date of Patent: *Dec. 12, 2023

(54) AUTOMATED WORKFLOW IN EMERGENCY MEDICAL SERVICES BILLING

(71) Applicant: ZOLL Medical Corporation, Chelmsford, MA (US)

(72) Inventors: Donna Magnuson, Arvada, CO (US); Lawrence Werner, Jr., Westminster, CO (US); Jason Haggstrom, Erie, CO (US); Justin Jacoby, Denver, CO (US)

(73) Assignee: ZOLL Medical Corporation, Chelmsford, MA (US)

( * ) Notice: Subject to any disclaimer, the term of this patent is extended or adjusted under 35 U.S.C. 154(b) by 261 days.

This patent is subject to a terminal disclaimer.

(21) Appl. No.: 17/183,060

(22) Filed: Feb. 23, 2021

(65) Prior Publication Data
US 2021/0241378 A1 Aug. 5, 2021

Related U.S. Application Data

(63) Continuation of application No. 15/471,310, filed on Mar. 28, 2017, now Pat. No. 10,970,785.

(60) Provisional application No. 62/315,902, filed on Mar. 31, 2016.

(51) Int. Cl.
*G06Q 40/08* (2012.01)
*G16H 10/60* (2018.01)
*G06Q 10/10* (2023.01)

(52) U.S. Cl.
CPC ............ *G06Q 40/08* (2013.01); *G06Q 10/10* (2013.01); *G16H 10/60* (2018.01)

(58) Field of Classification Search
CPC ...................................................... G16H 10/60
See application file for complete search history.

(56) References Cited

U.S. PATENT DOCUMENTS

| 6,542,905 | B1 | 4/2003 | Fogel et al. |
| 7,233,905 | B1 | 6/2007 | Hutton et al. |
| 7,734,481 | B1 | 6/2010 | Hutton et al. |
| 2001/0034618 | A1 | 10/2001 | Kessler et al. |

(Continued)

OTHER PUBLICATIONS

Notice of Allowance mailed in U.S. Appl. No. 15/471,310 dated Feb. 25, 2021.

(Continued)

*Primary Examiner* — John A Pauls
(74) *Attorney, Agent, or Firm* — Gardella Grace P.A.

(57) ABSTRACT

In one aspect, a system for automatically processing a medical claim includes a billing automation platform, a navigation device with a global positioning system for collecting patient transport information including a location of a medical encounter, and a computing device for receiving the patient transport information and patient charting information and transmitting the information for use by the billing automation platform. The billing automation platform may access fee schedule(s) based on a location of the medical encounter, automatically populate the medical claim based on the patient charting information, the patient transport information, and the fee schedule(s), and automatically route the medical claim through workflow paths of a claim processing workflow.

22 Claims, 6 Drawing Sheets

(56) References Cited

U.S. PATENT DOCUMENTS

| | | | |
|---|---|---|---|
| 2002/0133379 A1* | 9/2002 | Lewis | G06Q 10/10 |
| | | | 705/2 |
| 2004/0039623 A1* | 2/2004 | Setteducati | G06Q 10/06316 |
| | | | 705/7.24 |
| 2005/0261944 A1 | 11/2005 | Rosenberger | |
| 2006/0041487 A1* | 2/2006 | Santalo | G06Q 10/10 |
| | | | 705/30 |
| 2006/0259325 A1* | 11/2006 | Patterson | G16H 70/20 |
| | | | 705/2 |
| 2007/0033070 A1* | 2/2007 | Beck | G06Q 20/102 |
| | | | 705/40 |
| 2007/0203757 A1* | 8/2007 | Dibiasi | G06Q 40/08 |
| | | | 705/4 |
| 2011/0301972 A1* | 12/2011 | Baylor | G06Q 40/02 |
| | | | 705/2 |
| 2014/0188508 A1 | 7/2014 | DeFrank | |
| 2016/0342740 A1* | 11/2016 | Moore | G06Q 30/0202 |

OTHER PUBLICATIONS

Final Office Action mailed in U.S. Appl. No. 15/471,310 dated Jul. 14, 2020.

Non-Final Office Action mailed in U.S. Appl. No. 15/471,310 dated Mar. 20, 2020.

Final Office Action mailed in U.S. Appl. No. 15/471,310 dated Dec. 6, 2019.

Non-Final Office Action mailed in U.S. Appl. No. 15/471,310 dated Jun. 27, 2019.

ZOLL Data Systems, "RescueNet ePCR 5.4.3 Defect Release Notes," Jan. 26, 2014, (1 page) (Previously cited in related U.S. Appl. No. 15/471,310).

ZOLL Data Systems, "RescueNet ePCR Suite Administrator Guide," Software version 5.4.3, 2015, (389 pages) (Previously cited in related U.S. Appl. No. 15/471,310).

ZOLL Data Systems, "RescueNet Dispatch—Billing Upgrade Guide for Administrators," Oct. 16, 2015, (16 pages) (Previously cited in related U.S. Appl. No. 15/471,310).

ZOLL Data Systems, "RescueNet Dispatch—Billing 4.6 Services Install Guide," Oct. 23, 2015, (34 pages) (Previously cited in related U.S. Appl. No. 15/471,310).

ZOLL Data Systems, "RescueNet TabletPCR and WebPCR User Guide," Software Version 5.4.3, 2015 (205 pages) (Previously cited in related U.S. Appl. No. 15/471,310).

ZOLL Data Systems, "RescueNet Billing User's Guide," Software Version 4.6, 2015, (450 pages) (Previously cited in related U.S. Appl. No. 15/471,310).

ZOLL Data Systems, "RescueNet Dispatch—Billing Administration Guide," Release 4.6.1, Oct. 22, 2015 (740 pages) (Previously cited in related U.S. Appl. No. 15/471,310).

ZOLL Data Systems, "RescueNet Billing—Dispatch Release Notes," Software Version 4.6.1, Dec. 8, 2015 (5 pages) (Previously cited in related U.S. Appl. No. 15/471,310).

ZOLL Data Systems, "RescueNet Eligibility Services Installation Guide," Software Release 4.6, 2015 (7 pages) (Previously cited in related U.S. Appl. No. 15/471,310).

ZOLL Data Systems, "RescueNet ePCR 5.4.3 Feature Release Notes," Jan. 26, 2014, (1 sheet) (Previously cited in related U.S. Appl. No. 15/471,310).

\* cited by examiner

AUTOMATED WORKFLOW IN EMERGENCY MEDICAL SERVICES BILLING

CROSS-REFERENCE TO RELATED APPLICATIONS

This application is a continuation application of U.S. application Ser. No. 15/471,310 filed Mar. 28, 2017 entitled, "Automated Workflow In Emergency Medical Services Billing," now U.S. Pat. No. 10,970,785, which claims the benefit and priority of U.S. Provisional Patent Application Ser. No. 62/315,902, filed on Mar. 31, 2016. The above-identified applications are each hereby incorporated by reference in their entireties.

TECHNICAL FIELD

Embodiments of the present disclosure relate generally to automated workflow management, and more particularly, to methods and systems for facilitating efficient and streamline medical claims processing, as well as ensuring correct billing amount. Example embodiments can relate to EMS (emergency medical services).

BACKGROUND

It is often desirable to be able to efficiently and accurately process medical claims. Such efficient and accurate processing of medical claims enables a medical service provider to collect money soon after a medical service is provided. Efficient and accurate processing of medical claims also ensures that payers, such as insurance companies and patients, are billed correctly, such that they do not overpay or underpay.

From preparing claims for submission to payers, to payment received, claim processing may involve multiple steps. From one step to a next step, it typically requires a person to move forward the workflow process. For example, after a person verifies a claim, he or she proceeds to the next step (e.g., submit the claim to a payer or forward the claim to a personnel responsible for submitting the claim). The person may not know what the next step is, or may not know whom to forward the claim to. Or the person may delay the next step due to various reasons. For example, the person may be on vacation. Or she or he may be too busy to proceed to the next step. Dependency on a person to move forward the billing process may result in delays and errors.

In addition, determining the correct billing amount is sometimes challenging. Various factors need to be considered. Patients are typically responsible for their co-payments. Some patients have a deductible. In other words, those patients are responsible for the deductible amounts (e.g., $250 per year) which must often be met as a condition to the insurance company reimbursing for claim amounts beyond the deductible amount. However, some medical services that a patient receives do not invoke deductible payments. Sometimes, a patient may have more than one insurer. Accordingly, billing amounts need to be distributed to more than one payer. Patients may be eligible for insurance payments of some, not all, medical services that they receive. Payers may have agreements with service providers regarding payments. Some agreements are contractual. Payments may also depend on the locations that medical services are rendered. Due to the complexity of billing amount calculation, it may be error prone if a human is responsible for determining the correct billing amount.

SUMMARY

Techniques for automation of medical claim processing are disclosed. A system for automatically processing emergency medical claims according to an embodiment of the present disclosure includes: one or more processors and a memory, the memory containing instructions that, when executed by the processor, cause the processor to: receive an emergency medical claim; determine a status code corresponding to a current status of the claim and a reason code corresponding to a reason for the current status of the claim; and identify, based on the status code and the reason code, a task that needs to be completed on the claim and an administrator associated with the task.

In some cases, the memory further includes instructions that, when executed by the processor, further cause the processor to forward the claim to the administrator associated with the task.

In some cases, the administrator is a supervisor of the administrator associated with handing the task.

In some instances, the memory further includes instructions that, when executed by the processor, further cause the processor to further process payment of the claim upon completion of the task.

According to embodiments, the memory further includes instructions that, when executed by the processor, further cause the processor to identify an obstacle to normal processing the claim.

In one embodiment, the system further comprises a database storing status codes, reason codes, and workflow relations associated with each of the status codes and the reason codes, wherein each of the workflow relations is based on at least one of the associated status code and reason code, or a position in a workflow for processing the emergency medical claim.

In some cases, at least one of the status codes, reason codes, or the workflow relations are configurable through a user interface.

In some embodiments, the database further stores tasks associated with the status codes and the reason codes and administrators associated with the tasks.

According to some embodiments, the administrator associated with handling the task is configurable through a user interface.

The memory may further include instructions that, when executed by the processor, further cause the processor to query additional data for the claim, wherein the additional data comprises at least one of patient information, or intervention information.

A system for automatically processing emergency medical claims according to one embodiment of the present disclosure includes one or more processors and a memory, the memory containing instructions that, when executed by the processor, cause the processor to: receive an emergency medical claim; identify a first status code and a first reason code associated with the claim before a first task is completed for the emergency medical claim; confirm completion of the first task for the emergency medical claim; and determine, without human intervention, a second status code of the claim and a second reason code corresponding to a reason for the second status code for the claim, based on the first status code, the first reason code, and the first task.

In some instances, the memory further includes instructions that, when executed by the processor, further cause the processor to: automatically determine a second task based on the second status code and the second reason code; and automatically route the emergency medical claim from the first task to the second task.

In other instances, the memory further includes instructions that, when executed by the processor, further cause the processor to determine an administrator associated with the first task.

In some embodiments, the memory further includes instructions that, when executed by the processor, further cause the processor to automatically forward the claim to the administrator associated with the first task.

In some instances, the first task comprises an order import task configured to import the emergency medical claim; and the second task comprises a needs verification task configured to validate the emergency medical claim.

According to some embodiments, the first task comprises a ready for submission task configured to submit the emergency medical claim for billing; and the second task comprises a submitted bill task configured to manage the emergency medical claim after being submitted for billing.

In some embodiments, the first task comprises a payment posted task configured to manage emergency medical claims associated with whole or partial payments; and the second task comprises a closed task terminating the processing of the emergency medical claim.

According to some embodiments, the first status code comprises a follow-up status indicating that the emergency medical claim requires follow-up; the first reason code comprises a no response reason code indicating that the emergency medical claim has been submitted for payment but no payment has been received for the emergency medical claim; and the first task comprises a follow-up task configured to automatically route the emergency medical claim to an associated administrator for follow-up.

According to some embodiments, the first status code comprises a denied status indicating that the claim was denied for payment; the first reason code indicates that the claim was denied in full for payment; and the first task comprises a denied task configured to automatically route the emergency medical claim to an administrator associated with denied claims for rebilling.

A system for automatically processing emergency medical claims according to some embodiments of the present disclosure includes one or more processors and a memory, the memory containing instructions that, when executed by the processor, cause the processor to automatically: receive a medical claim; determine a current status of the medical claim and a reason for the current status of the medical claim; identify a task that needs to be completed on the medical claim; and forward the medical claim to an administrator associated with the task.

A system for automatically processing emergency medical claims according to some embodiments of the present disclosure includes: a payer plan database storing payer plan information; one or more processors, a memory, the memory containing instructions that, when executed by the processor, cause the processor to: receive an emergency medical claim; identify a payer of the claim; look up a payer plan amount in the payer plan database; and adjust the claim based on the payer plan amount.

In some cases, the payer plan database is configured to store data populated based on contractual terms for the payer.

In some embodiments, the memory further includes instructions that, when executed by the processor, further cause the processor to adjust the claim if a status of the claim indicates a payment of the claim has been posted with a payment discrepancy between the payment posted and a payment amount in the claim.

According to some embodiments, the memory further includes instructions that, when executed by the processor, further cause the processor to adjust the claim if a payment of the claim is not received within a time period after the claim is submitted to the payer.

In some instances, the memory further includes instructions that, when executed by the processor, further cause the processor to write-off the claim and forward the claim to an outside collection agency.

A system for automatically processing emergency medical claims according to embodiments of the present disclosure includes one or more processors and a memory, the memory containing instructions that, when executed by the processor, cause the processor to: receive an emergency medical claim; identify a payer of the claim; and determine an amount to be collected from the payer, e.g., based on a payment schedule of the payer, wherein the payment schedule of the payer is associated with a third party.

In some cases, the third party is at least one of Medicare or Medicaid.

According to some embodiments, the one or more processors are further configured to update the payment schedule of the payer according to a payment schedule update of the third party.

A system for automatically processing emergency medical claims according to embodiments of the present disclosure includes one or more processors and a memory, the memory containing instructions that, when executed by the processor, cause the processor to: receive an emergency medical claim; identify a payer of the claim; and determine an amount to be collected from the payer, e.g., based on a past payment of the payer for a same type of claim.

In some instances, the memory further includes instructions that, when executed by the processor, further cause the processor to submit the emergency medical claim to the payer for payment.

According to some embodiments, the memory further includes instructions that, when executed by the processor, further cause the processor to adjust the amount to be collected from the payer if there are a plurality of payers for the claim.

In some cases, the memory further includes instructions that, when executed by the processor, further cause the processor to adjust the amount to be collected from the payer based on at least one of patient eligibility, patient co-payment, patient deductible, or patient co-insurance.

According to some embodiments, the memory further includes instructions that, when executed by the processor, further cause the processor to adjust the amount to be collected from the payer based on a payment schedule of the payer, wherein the payment schedule of the payer is associated with a third party.

In some instances, the memory further includes instructions that, when executed by the processor, further cause the processor to determine a collection risk of the amount to be collected.

According to some embodiments, the memory further includes instructions that, when executed by the processor, further cause the processor to determine an amount that has been received from the payer and identify a discrepancy between the amount to be collected and the amount that has been received.

Figure 1:
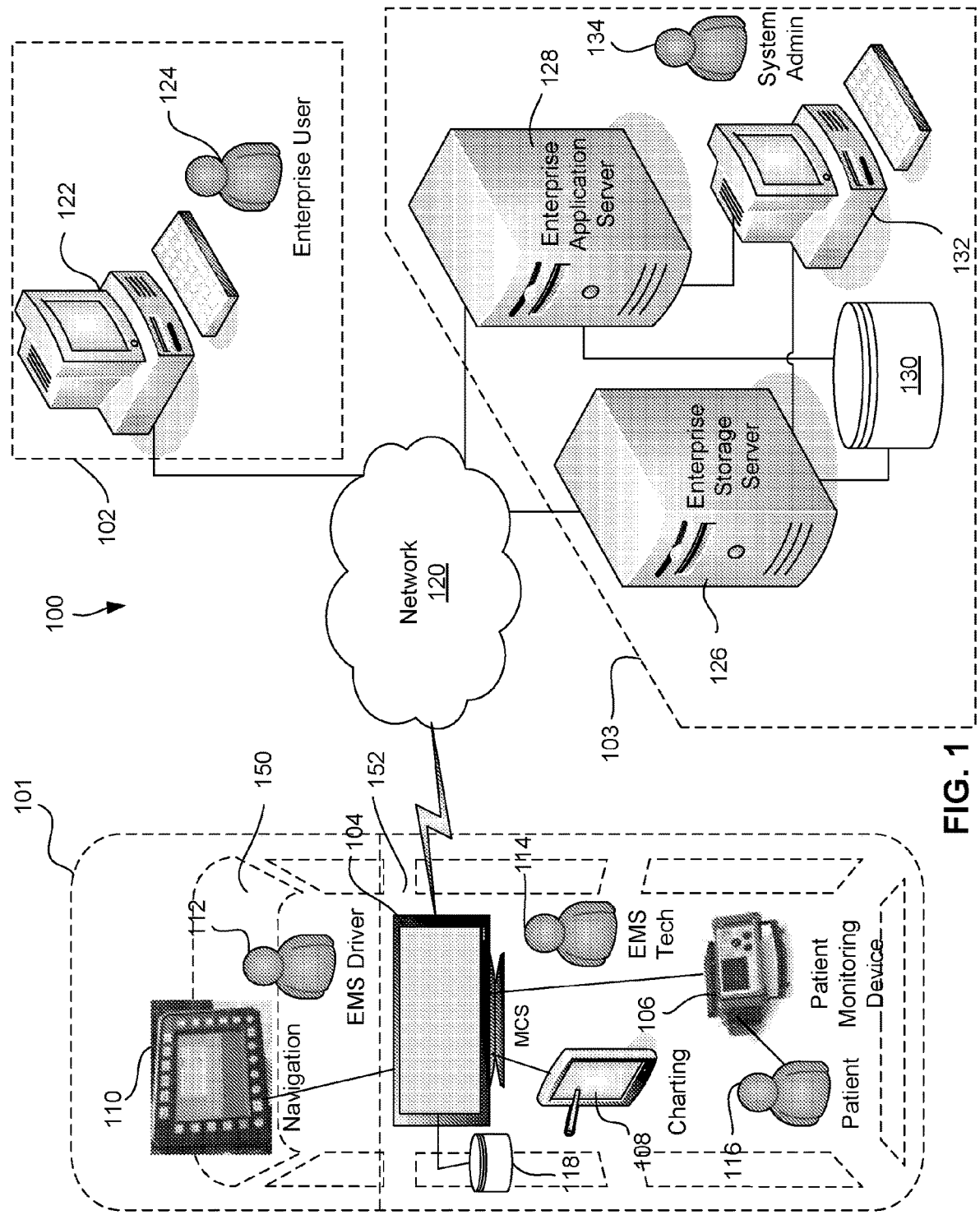
FIG. 1 illustrates a system for mobile and enterprise real-time display of medical information collected from multiple different EMS devices, according to some embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Efficient and accurate medical billing is important. It ensures that service providers receive payment for the services they provide. If a service provider fails to collect payments for the services it provides, the service provider may not be able to continue to operate due to lack of funds. Efficient and accurate medical billing also helps to ensure that patients and/or payers (e.g., insurance companies, Medicare and Medicaid) do not overpay or under-pay. Incorrect billing will result in administrative overhead and payment delay. In some embodiments, predicting payment expectation assists in identifying those times when a payer or a patient under-pays or over-pays; often times, this cannot be prevented, but using processes that predict and/or identify payment amount discrepancies can provide better notifications to the users of a medical billing system, and/or better route such claims through a workflow in a manner that permits more detailed review of under- or over-payment aspects of processing. Systems without this functionality may be more prone to human error when a payment poster must identify whether the payment is correct and manually route the claim accordingly.

For example, claim denial and resubmission may increase claim processing cost. As used herein, the term "claim" is used in its broadest sense to refer to a request, either electronic or physical, for payment or reimbursement. A claim may be a medical claim, in other words a claim for reimbursement or payment of expenses associated with a medical procedure, encounter, or visit. An emergency medical claim is a claim for reimbursement or payment of expenses associated with an emergency medical procedure, encounter, or visit.

Claim processing involves multiple steps and billing amount determination is complex. Human processing may be slow and error-prone.

It may be desirable that claim processing is automated. For example, once a service order has been created and/or a medical service has been rendered, a claim of the medical service is automatically created, with claim data populated and the claim forwarded to administrator responsible for verifying the claim. Once the administrator (for example, an administrator that is a biller) verifies the claim, it may be desirable that the claim's status is updated as "ready for submission" and forwarded to an administrator responsible to submit the claim to the one or more payers (for example, an administrator that is a clearinghouse).

Some embodiments of the present disclosure include systems, apparatus, and methods for automating medical claim processing. In some embodiments, a medical claim is analyzed. A current status of the claim may be determined. The current status may indicate where the claim stands in the billing process. The current status may be, for example, order import, follow up, suspend bill, and/or payment posted. A reason for the current status of the claim may be determined. The reason may indicate why the claim is in the current status. For example, the reason may be: needs verification, no response for invoice, and/or payer paid patient. Based on the current status and the reason for current status of the claim, a role for the claim may be determined. The reason may indicate a task to be completed on the claim. The role may identify a function of an administrator member (e.g. an administrator with a billing function) or department who is responsible for handling the claim after it leaves a particular node or step. For example, if the role is "authorizations," the claim may be forwarded to the authorization department or group.

Other embodiments of the present disclosure include systems, apparatus, and methods for determining a billing amount for a claim or checking the accuracy of a billing amount of a claim. A payer responsible for the payment of the claim may be determined. The billing amount may be determined or checked for accuracy based on past occurrence and/or payment history of the payer for same or similar type claims. For example, if the claim is for ambulatory transportation to an urgent care facility, and the payer pays X dollar amount in the past for such services, then the billing amount for the claim will be determined as X dollar amount. In some embodiments, if past occurrence and/or payment history for the same type claim associated with the payer is not available, then the billing amount may be determined or checked for accuracy based on a similar type claim. For example, no past occurrence and/or history payment of the payer for ambulatory transportation to an urgent care facility is available, but past occurrence and/or history payment of the payer for ambulatory transportation to a skilled nursing facility is available, then the billing amount of the claim is determined based on payer's past occurrence and/or payment history of ambulatory transportation to a skilled nursing facility (e.g., Y dollar amount). As used herein, the term "payer" is used in its broadest sense to refer to any person or entity who pays, or is obligated to pay, or who might pay all or part of a claim, for example a claim for billing of emergency medical services. The payer may have a plan, which may otherwise be known as a contract, agreement, or course of conduct reflecting how it approves payment of claims; this may be referred to as a payer plan. For example, in one simple payer plan, the payer agrees to pay 80% of all medical claims after a deductible of $1000 has been paid by the patient with whom the payer offers the payer plan.

Yet other embodiments of the present disclosure include systems, apparatus, and methods for determining a billing amount of a payer for a claim based on a fee schedule of a third party. For example, a payer may tie its fee schedule to that of Medicare and pays certain percentage (e.g., 90% or 110%) of the Medicare payment schedule for same or similar type claims. A fee schedule sets forth amounts and/or percentages of reimbursement or payment for various types of services or costs.

Yet other embodiments of the present disclosure include systems, apparatus, and methods for workflow automation. In some embodiments, a work item may be received. A current status of the work item and a reason for the current status of the work item may be determined. A task that needs to be completed on the workflow item may be identified. The work item may be forwarded to an administrator (e.g. a biller or other administrator) responsible for handling the task.

As illustrated in FIG. 1, a system 100 according to some embodiments performs advanced data management, integration and presentation of EMS data from multiple different devices. Emergency medical services billing automation systems described in detail throughout the present disclosure may interact with system 100 for patient information, services rendered or services to be authorized. System 100 includes a mobile environment 101, an enterprise environment 102, and an administration environment 103. Devices within the various environments 101, 102, 103 may be communicably coupled via a network 120, such as, for example, the Internet.

While the emergency medical services billing automation and audit systems described herein may be implemented in hardware, software, or a combination thereof, as well as implemented on one device or a combination of devices or from a server-based implementation, FIG. 1 and its related description is provided as merely one non-limiting example of a system and devices that may be used to send, receive, and/or gather information about an EMS encounter for which a billing or reimbursement claim would be submitted. In one embodiment, a billing automation platform such as those described herein may be implemented on enterprise storage server 126 and/or enterprise application server 128, which in some cases may be the same servers that directly or indirectly acquire data about a particular encounter from MCS device 104 and/or other devices such as 106, 108, 110, and other devices. In some embodiments, a billing automation platform is one of multiple server-based services implemented via servers 126 and/or 128, such that the billing automation platform can access information from or about emergency dispatch, patient encounters, transports, enterprise user 124 activities, and/or the like.

As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network, or direct coupling.

According to embodiments of the present disclosure, the mobile environment 101 is an ambulance or other EMS vehicle—for example a vehicular mobile environment (VME). The mobile environment may also be the local network of data entry devices as well as diagnostic and therapeutic devices established at time of treatment of a patient or patients in the field environment, such as an "At Scene Patient Mobile Environment" (ASPME). The mobile environment may also be a combination of one or more of VMEs and/or ASPMEs. The mobile environment may include a navigation device 110 used by the EMS driver 112 to track the mobile environment's 101 position, locate the mobile environment 101 and/or the emergency location, and locate the transport destination, according to embodiments of the present disclosure. The navigation device 110 may include a Global Positioning System ("GPS"), for example. The navigation device 110 may also be configured to perform calculations about vehicle speed, the travel time between locations, and estimated times of arrival. According to embodiments of the present disclosure, the navigation device 110 is located at the front of the ambulance to assist the EMS driver 112 in navigating the vehicle. The navigation device 110 may be, for example, a RescueNet® Navigator onboard electronic data communication system available from Zoll Data Systems of Broomfield, Colo.

As illustrated in FIG. 1, a patient monitoring device 106 and a patient charting device 108 are also often used for patient care in the mobile environment 101, according to embodiments of the present disclosure. An EMS technician 114 attaches the patient monitoring device 106 to a patient 116 to monitor the patient 116. The patient monitoring device 106 may be, for example, a defibrillator device with electrodes and/or sensors configured for attachment to the patient 116 to monitor heart rate and/or to generate electrocardiographs ("ECG's"), according to embodiments of the present disclosure. The patient monitoring device 106 may also include sensors to detect or a processor to derive or calculate other patient conditions. For example, the patient monitoring device 106 may monitor, detect, treat and/or derive or calculate blood pressure, temperature, respiration rate, blood oxygen level, end-tidal carbon dioxide level, pulmonary function, blood glucose level, and/or weight, according to embodiments of the present disclosure. The patient monitoring device 106 may be a ZOLL E-Series®, X-Series®, R-Series®, or other defibrillator available from ZOLL Medical Corporation of Chelmsford, Mass., according to embodiments of the present disclosure. A patient monitoring device may also be a patient treatment device, or another kind of device that includes patient monitoring and/or patient treatment capabilities, according to embodiments of the present disclosure. For example, if the patient monitoring device is a defibrillator, the patient monitoring device can also deliver therapeutic electric shocks to the patient. In other embodiments, the patient monitoring device can also deliver other types of treatments, such as operating a respirator, or administering drugs or other medication.

The patient charting device 108 can be a device used by the EMS technician 114 to generate records and/or notes about the patient's 116 condition and/or treatments applied to the patient, according to embodiments of the present disclosure. For example, the patient charting device 108 may be used to note a dosage of medicine given to the patient 116 at a particular time. The patient charting device 108 and/or patient monitoring device 106 may have a clock, which may be synchronized with an external time source such as a network or a satellite to prevent the EMS technician from having to manually enter a time of treatment or observation (or having to attempt to estimate the time of treatment for charting purposes long after the treatment was administered), according to embodiments of the present disclosure. The patient charting device 108 may also be used to record biographic and/or demographic and/or historical information about a patient, for example the patient's name, identification number, height, weight, and/or medical history, according to embodiments of the present disclosure. According to embodiments of the present disclosure, the patient charting device 108 is a tablet PC, such as for example the TabletPCR component of the RescueNet® ePCR Suite available from ZOLL Data Systems of Broomfield, Colo.

According to some embodiments of the present disclosure, the patient charting device 108 is a wristband or smart phone such as an Apple iPhone or iPad with interactive data entry interface such as a touch screen or voice recognition data entry that may be communicably connected to the MCS device 104 and tapped to indicate what was done with the patient 116 and when it was done. According to some embodiments of the present disclosure, the patient charting device 108 can be integrated with the patient monitoring device 106, such that a single device can be configured to monitor the patient, treat the patient, as well as to generate records and/or notes about the patient's 116 condition and/or treatments applied to the patient.

The navigation device 110, the patient charting device 108, and the patient monitoring device 106 are each separately very useful to the EMS drivers 112 and EMS technicians 114 before, during, and after the patient transport. A "mobile computing system" ("MCS") device 104 may receive, organize, store, share, distribute, and/or display data from each device 106, 108, 110 to further enhance the usefulness of each device 106, 108, 110 and to make it much easier for the EMS technician 114 to perform certain tasks that would normally require the EMS technician 114 to divert visual and manual attention to each device 106, 108, 110 separately, according to embodiments of the present disclosure. In other words, the MCS device 104 centralizes, organizes, and shares information that would normally be de-centralized and disorganized, according to embodiments of the present disclosure.

Although the MCS device 104 is referred to herein as a "mobile computing system" device because the EMS technician 114 would normally benefit the most from having such a display device mounted in the back 152 of an ambulance or vehicle or other mobile operation, one of ordinary skill in the art, based on the disclosure provided herein, will recognize that some or all of the MCS device 104 may be located in any part of a mobile environment 101, EMS vehicle, and/or anywhere else useful to an EMS technician 114. For example, the MCS device 104 may be located in the front 150 of an ambulance, and/or may include components that are portable and can be carried into a patient residence, according to embodiments of the present disclosure.

The MCS device 104 is communicably coupled to the patient monitoring device 106, the patient charting device 108, and the navigation device 110, according to embodiments of the present disclosure. The MCS device 104 is also communicably coupled to a storage medium 118. The MCS device 104 may be a touch-screen, flat panel PC, and the storage medium 118 may be located within or external to the MCS device 104, according to embodiments of the present disclosure. The MCS device 104 may include a display template serving as a graphical user interface, which permits the user (e.g. EMS tech 114) to select different subsets and/or display modes of the information gathered from and/or sent to the devices 106, 108, 110, according to embodiments of the present disclosure.

According to embodiments of the present disclosure, the MCS device 104 not only seamlessly integrates information from a patient monitoring device 106, a patient charting device 108, and a navigation device 110 for display in mobile environment 101, but it also does so for display in a remote environment such as, for example, enterprise environment 102. Enterprise environment 102 may be a hospital and/or dispatch environment, for example.

Data from the MCS device 104 (and therefore data from the devices 106, 108, 110 communicably coupled with the MCS device 104) may be received by one or more enterprise storage servers 126 in an administration environment 103 and stored in an enterprise database 130, and the same information may be accessed and provided by one or more enterprise application servers 128 to an enterprise workstation 122 of an enterprise user 124, according to embodiments of the present disclosure. According to embodiments of the present disclosure, the MCS device 104 is communicably coupled to the enterprise storage server 126 which is communicably coupled to the enterprise database 130, and the enterprise application server 128 is communicably coupled to the enterprise database and to the enterprise workstation 122. Such devices may be communicably coupled via a network 120 such as, for example, the Internet.

When the MCS device 104 receives updated information from one or more of the devices (e.g. devices 106, 108, 110) to which it is communicably coupled, the MCS device 104 sends the updated information to the enterprise storage server 126, which stores the updated information in a database which may be contained on a storage medium 130, according to embodiments of the present disclosure. Hence, information from one or more devices (e.g. devices 106, 108, 110) may be stored in mobile database 118, remote enterprise database 130, or both, according to embodiments of the present disclosure. An enterprise user 124, who may be an emergency room nurse monitoring and/or preparing for ambulance arrivals, an emergency room physician, and/or a medical director at home, for example, may access information similar to information displayed by the MCS device 104 by requesting the information via an enterprise workstation 122. For example, the enterprise workstation 122 accesses a web interface and/or thin client web browser application which requests the information over the network 120 from the enterprise application server 128. The enterprise application server 128 queries the enterprise database 130 for the information, and returns a display to the enterprise workstation 122 that looks the same as or similar to what the EMS technician 114 is currently seeing on the MCS device 104 display, according to embodiments of the present disclosure.

The MCS device 104 can also share information with one or more of the devices (e.g., devices 106, 108, 110). For example, information generated from one of the devices 106, 108, and/or 110 can be collected and then shared with one or more of the other devices. The MCS device 104 can also receive information from enterprise application server 128, and/or enterprise storage server 126, and either display such information itself, or share such information with devices 106, 108, and/or 110. For example, if patient monitoring device 106 takes an ECG reading of a patient 116, or if the patient monitoring device 106 administers a treatment (such as medication or a defibrillation shock), the ECG reading and/or treatment can be shared, via MCS device 104 or directly, with patient charting device 108 for storage in a patient record maintained therein. In another example, MCS device 104 can be configured to receive patient information, such as medical records, known medical conditions, and biographical information, and to share this information with devices 106, 108, and/or 110. This biographical information can be inserted into a patient record being maintained in patient charting device 108. Alternatively, this biographical information can be used to inform a treatment being administered by patient monitoring device 106, and/or navigation data displayed by navigation device 110.

Although FIG. 1 depicts a single MCS device 104 in the mobile environment 101, more than one MCS device 104 may be used in the mobile environment 101 to communicably connect to the same or a different set of devices 106, 108, 110. And although FIG. 1 depicts one mobile environment 101, more than one mobile environment 101 and/or more than one MCS device 104 may be communicably coupled with the administration environment 103 and/or the enterprise storage server 126, according to embodiments of the present disclosure. According to embodiments of the present disclosure, the enterprise storage server 126 receives EMS device information from MCS device 104 and stores it in enterprise database 130 along with an authenticated time stamp and an identifier associating the information with a particular EMS device and/or a particular EMS vehicle. In this way, data from multiple vehicles and/or multiple devices may be accessed by the enterprise user 124.

Also, the enterprise storage server 126 may securely store the information received from one or more MCS devices 104 for longer periods of time to permit later use of the information. For example, the MCS device 104 may receive patient-identifying information such as name, address, and/or social security number via the patient charting device 108 or directly through the MCS device 104, and then may convey some or all of the patient-identifying information to enterprise storage server 126 with a request for the enterprise storage server 126 to query the enterprise database 130 for past records involving the same patient 116. The enterprise storage server 126 may then forward any such records or portions of such records back to the MCS device 104 (e.g. for display in the patient charting screen or the Past Medical History in the patch notes screen) to assist the EMS technician 114 with the current emergency. Similarly, such past EMS encounter record information may also be accessed by the enterprise user 124, according to embodiments of the present disclosure. A system administrator 134 may access and/or monitor the data in enterprise database 130 and/or modify the instructions of the servers 126, 128 via administration workstation 132, which may be communicably coupled to the servers 126, 128, according to embodiments of the present disclosure.

According to some embodiments of the present disclosure, the MCS device 104 may connect with (e.g. automatically or manually or selectively) a wearable medical device, such as, for example, a Lifevest® wearable defibrillator, to receive and display patient monitoring information therefrom. The MCS device 104 may also be configured to receive patient-identifying information from such a wearable device, to permit the MCS device 104 to query an external database, for example across network 120, to retrieve additional information about the patient 116. The MCS device 104 may also be configured to connect with an implantable cardioverter-defibrillator ("ICD") in a similar fashion, according to embodiments of the present disclosure.

Further details regarding system 100 can be found in US Patent Application Publication No. 2011/0172550, titled "SYSTEMS AND METHODS FOR EMS DEVICE COMMUNICATION INTERFACE," published Jul. 14, 2011, the entire contents of which are incorporated herein by reference.

Some embodiments include various steps, some of which may be performed by hardware components or may be embodied in machine-executable instructions. These machine-executable instructions may be used to cause a general-purpose or a special-purpose processor programmed with the instructions to perform the steps. Alternatively, the steps may be performed by a combination of hardware, software, and/or firmware. In addition, some embodiments of the present invention may be performed or implemented, at least in part (e.g., one or more modules), on one or more computer systems, mainframes (e.g., IBM mainframes such as the IBM zSeries, Unisys ClearPath Mainframes, HP Integrity NonStop servers, NEC Express series, and others), or client-server type systems. In addition, specific hardware aspects of embodiments of the present invention may incorporate one or more of these systems, or portions thereof.

Figure 2:
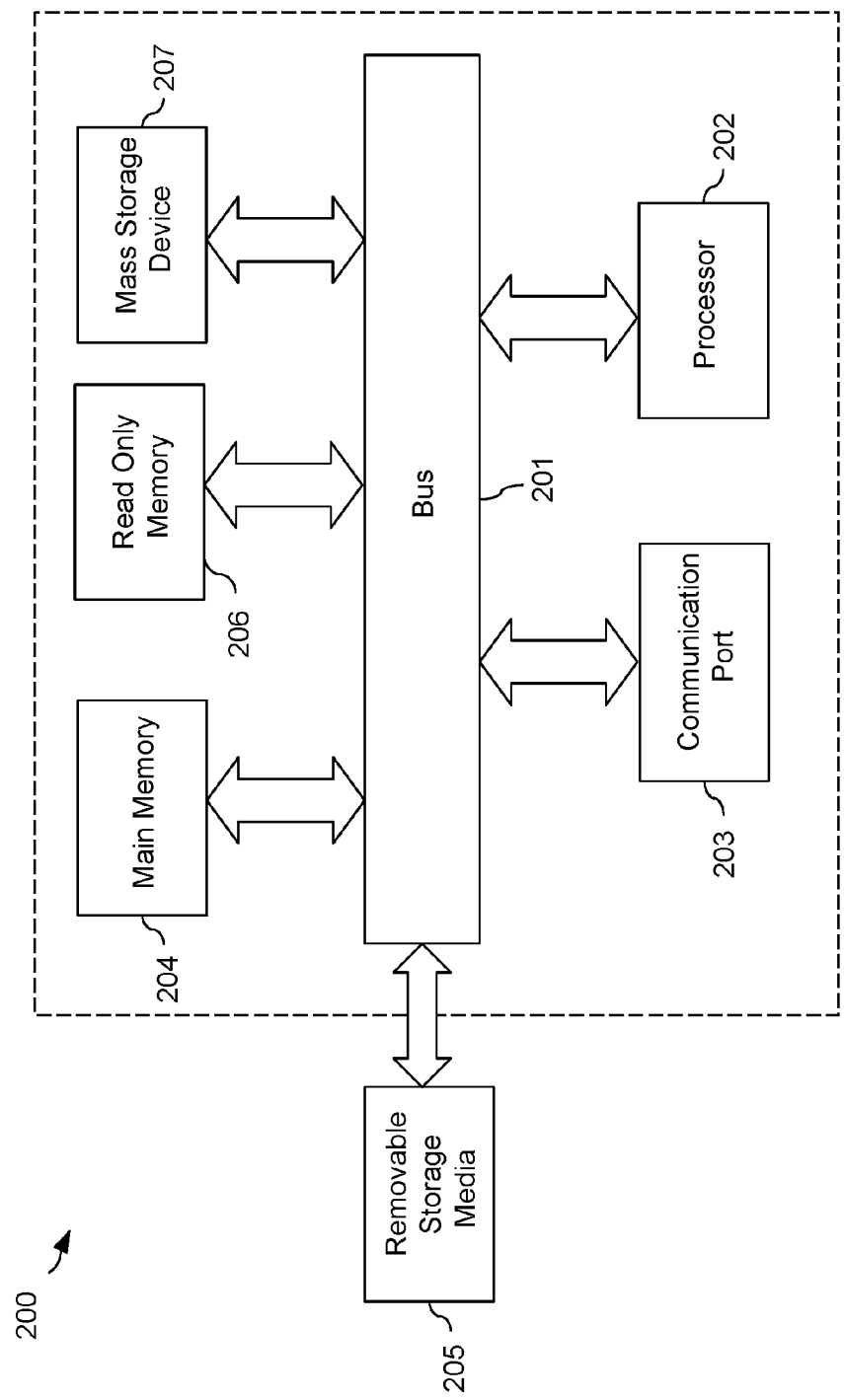
FIG. 2 is an example of a computer system 200 with which embodiments of the present invention may be utilized.

As such, FIG. 2 is an example of a computer system 200 with which embodiments of the present invention may be utilized. According to the present example, the computer system includes a bus 201, at least one processor 202, at least one communication port 203, a main memory 204, a removable storage media 205, a read only memory 206, and a mass storage 207.

Processor(s) 202 can be any known processor, such as, but not limited to, an Intel® Itanium® or Itanium processor(s), or AMD® Opteron® or Athlon MP® processor(s), or Motorola® lines of processors. Communication port(s) 203 can be any of an RS-232 port for use with a modem based dialup connection, a 10/100 Ethernet port, or a Gigabit port using copper or fiber, for example. Communication port(s) 203 may be chosen depending on a network such a Local Area Network (LAN), Wide Area Network (WAN), or any network to which the computer system 200 connects. Main memory 204 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, hard disks such as the Adaptec® family of SCSI drives, an optical disc, an array of disks such as RAID (e.g. the Adaptec family of RAID drives), or any other mass storage devices may be used, for example. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, flash drives, IOMEGA® Zip Drives, Compact Disc-Read Only Memory (CD-ROM), Compact Disc-Re-Writable (CD-RW), or Digital Video Disk-Read Only Memory (DVD-ROM), for example. The components described above are meant to exemplify some types of possibilities. In no way should the aforementioned examples limit the scope of the invention, as they are only exemplary embodiments.

Figure 3:
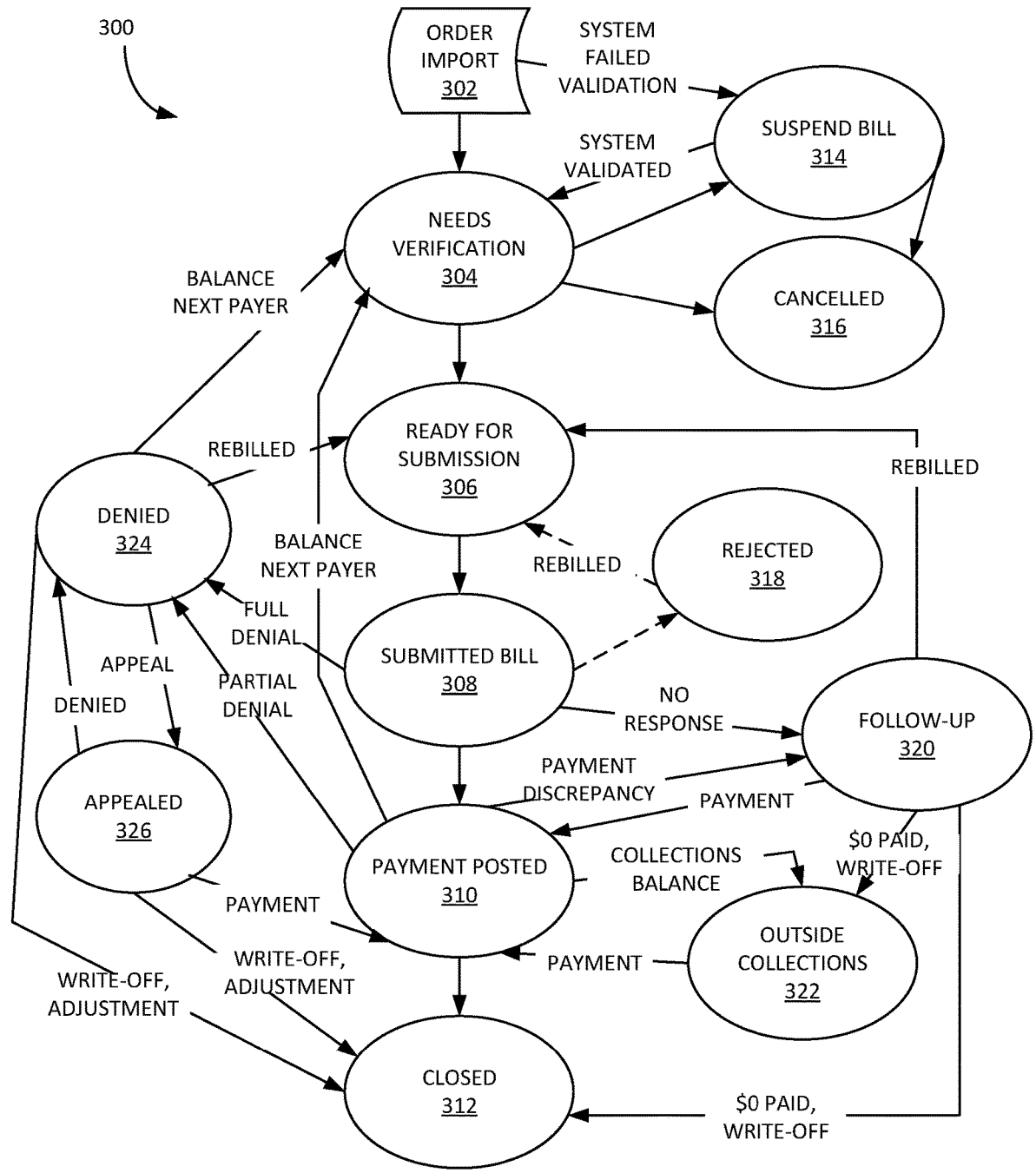
FIG. 3 illustrates an example workflow diagram for medical claim processing.

FIG. 3 illustrates an example workflow diagram for medical claim processing. The example includes various steps, one or more of which may be performed by hardware components described herein, such as a processor, or may be embodied in machine-executable instructions, and performed automatically and without human intervention. As shown in FIG. 3, claim processing may include multiple steps. Claim processing 300 may start at order import 302 and end at closed 312. In between, the normal processing steps may include needs verification 304, ready for submission 306, submitted bill 308, payment posted 310. In some embodiments, if all needed information is populated on a claim and a payer pays the amount indicated on the claim, the claim processing starts blocks 302, proceeds through blocks 304, 306, 308, 310, and finally ends at block 312. However, a claim may proceed through extra steps for various reasons, such as claim data is incomplete, payers do not pay, or payers do not pay the amount indicated on the claim. Accordingly, extra steps may include, but not limited to, suspend bill 314, cancelled 316, rejected 318, follow up 320, outside collection 322, denied 324, and appealed 326.

Each step/node in the process 300 may present a current status of a claim. For example, a claim may have a current status of needs verification 304. The current status of a claim represents where the claim is in the billing process. In some embodiments, as will be described with further details in subsequent sections, each claim may be associated with a current status of a claim and a reason for the current status of the claim.

As used herein, the term "code" is used in its broadest sense to refer to a state identifier or contents of a field, whether numeric, alphanumeric, text, or otherwise, that can be differentiated from other codes. A code may be contained within a claim or an electronic representation of a claim; alternatively, a code may be stored remotely and/or associated with a claim but not be part of the claim, in some embodiments. For example, a status code is a field or state identifier that represents a status for a claim; it may be numeric, alphanumeric, text, or otherwise. The status code indicates a status of a claim; different claims may have the same status code, and different status codes may be applied to the same claim throughout its processing. According to some embodiments, more than one status code exists for claims processing, and the one or more systems that route and/or process the claim can distinguish between the different status codes to identify or associate a current status to the claim, and/or to identify a prior status or assign a next status code. As shown below, examples of status codes for a claim, such as an emergency medical services claim, include "follow up" which means that the claim needs further action prior to payment or finalization, and another example includes "denied" indicating that the claim has been or is being denied payment, for example by the payer or the proposed payer.

A reason code is a field or state identifier that represents a reason for a claim; it may be numeric, alphanumeric, text, or otherwise. The reason code indicates a reason why the claim has the status that it has; different claims may have the same reason code, and different reason codes may be applied to the same claim throughout its processing. According to some embodiments, more than one reason code exists for claims processing, and the one or more systems that route and/or process the claim can distinguish between the different reason codes to identify or associate a current reason to the claim, and/or to identify a prior reason or assign a next reason code. Examples of reason codes for a claim, such as an emergency medical services claim, are shown below.

Based on the current status and the reason, each claim may be associated with a role. In some embodiments, role is an indication of the administrator who is responsible for handling the claim after it leaves the node. There may be multiple reasons and/or roles associated with a status. After the administrator handles the claim, the claim may be assigned a different status and role and ready for further processing. An exemplary list of reasons and roles associated with status "Follow up" 320 is listed in Table 1. An exemplary list of reasons and roles associated with status "Denied" 324 is listed in Table 2.

TABLE 1

An exemplary list of reasons and roles associated with status "Follow up."

| Status | Reason | Role |
|---|---|---|
| Follow-up | Account review | Payer follow-up |
| Follow-up | Adjustment (not posted) | none |
| Follow-up | Adjustment rejected | Payer follow-up |

TABLE 1-continued

An exemplary list of reasons and roles associated with status "Follow up."

| Status | Reason | Role |
|---|---|---|
| Follow-up | Adjustment requested | Payer follow-up |
| Follow-up | Balance after adjustment | Payer follow-up |
| Follow-up | Balance after refund | Payer follow-up |
| Follow-up | Balance forwarded | Payer follow-up |
| Follow-up | Bill date > Date of death | Payer follow-up |
| Follow-up | Bill date > end of use date | Payer follow-up |
| Follow-up | Clinical documentation requested | none |
| Follow-up | Collections review | Payer follow-up |
| Follow-up | Credit balance | Payer follow-up |
| Follow-up | Date of service changed | Payer follow-up |
| Follow-up | Deductible variance | Payer follow-up |
| Follow-up | Doctor not enrolled in PECOS | none |
| Follow-up | End of use pending | Payer follow-up |
| Follow-up | Facility balance | Payer follow-up |
| Follow-up | LOA overpayment | Payer follow-up |
| Follow-up | LOA underpayment | Payer follow-up |
| Follow-up | No response {0} invoice | Payer follow-up |
| Follow-up | No response 1st invoice | none |
| Follow-up | No response 2nd invoice | none |
| Follow-up | No response 3rd invoice | none |
| Follow-up | No response 4th invoice | none |
| Follow-up | No response 5th invoice | none |
| Follow-up | No response from payer | Payer follow-up |
| Follow-up | Offset pending | Payer follow-up |
| Follow-up | Overpayment | Payer follow-up |
| Follow-up | Patient involvement needed | none |
| Follow-up | Payer offset | Payer follow-up |
| Follow-up | Payer paid the patient | Patient follow-up |
| Follow-up | Payer reprocessing | Payer follow-up |
| Follow-up | Payment (not posted) | Payer follow-up |
| Follow-up | Payment date > end of use date | Payer follow-up |
| Follow-up | Payment from terminated insurance | Payer follow-up |
| Follow-up | Payment move requested | none |
| Follow-up | Payment plan not met | Payer follow-up |
| Follow-up | Payment promised | none |
| Follow-up | Payment reversal | Payer follow-up |
| Follow-up | Reconsideration | none |
| Follow-up | Refund requested | none |
| Follow-up | Review requested | Payer follow-up |
| Follow-up | Senior follow-up review | Payer follow-up |
| Follow-up | Un-adjudicated | Payer follow-up |
| Follow-up | Underpayment | Payer follow-up |
| Follow-up | Verify COB | Coordination of benefits |
| Follow-up | Write-off (not posted) | none |

TABLE 2

An exemplary list of reasons and roles associated with status "Denied."

| Status | Reason | Role |
|---|---|---|
| Denied | Adjustment (not posted) | none |
| Denied | Adjustment rejected | Denials |
| Denied | Adjustment requested | Denials |
| Denied | Appeal needed | Appeals |
| Denied | Balance after adjustment | Denials |
| Denied | Date of service changed | Denials |
| Denied | Denial unresolved | Denials |
| Denied | Denial upheld | Appeals |
| Denied | End of use pending | Denials |
| Denied | Full denial | Denials |
| Denied | Offset pending | Denials |
| Denied | Partial denial | Denials |
| Denied | Payer reprocessing | Denials |
| Denied | Payment (not posted) | Denials |
| Denied | Write-off (not posted) | none |

As used herein, "administrator" is used in its broadest sense to refer to a person or entity or group of people or entities that are associated with making decisions or performing tasks associated with processing of the claim. An administrator may be an employee, staff member, contractor, claims processing entity or service, supervisor, and/or department, according to some embodiments. An administrator may also be a supervisor and/or a delegate or subordinate employee or designate, according to some embodiments.

A role code is a field or state identifier that represents a role associated with one or a combination of the status code and the reason code; it may be numeric, alphanumeric, text, or otherwise. The role code indicates a role associated with the administrator who performs the task or tasks associated with the claim in order for the claims processing system to continue routing the claim through the system. The particular administrator or administrators associated with a given role code may be dynamically modified and/or customized over time. The role code indicates to which administrator (or node illustrated in FIG. 3) the claim should be routed, without human intervention (i.e. without any person needing to decide where to route the claim). As illustrated above, the claims processing system may include one or more tables associating status and reason codes with role codes, according to some embodiments. Such tables may be customized and/or adjusted over time, according to some embodiments. Examples of roles or role codes are also shown, above, according to some embodiments.

For example, a claim may be in current status of follow-up 320 and the reason for the current status is "No response {0} invoice" (i.e., the claim has been submitted to the payer once, but the payer has not responded). Based on the current status and the reason associated with the claim, a role for the claim may be determined. In some embodiments, the role identifies a function of administrator member or department who is responsible for handling the claim. The role may then be mapped to at least one administrator or department that is responsible for handling the task for the claim. A task is an action or process to be performed for further processing of the claim, and may include steps to be performed by an administrator (e.g. a person and/or a device) before the claim is be further routed through the process of FIG. 3. As explained above, a task may be associated with a particular role code, and/or a combination of a status code, a reason code, and/or a role code. For example, based on the current status "follow up" and the reason "No response {0} invoice," the role "payer follow-up" may be determined. Based on the role "payer follow-up," the claim may be forwarded to an administrator member who is responsible for "payer follow-up." By way of example, the administrator member may complete the task "payer follow-up" by re-billing the claim or by writing-off the claim. Depending on the completed task, the claim is processed further. If the claim is re-billed, the claim will then be in a status of ready-for submission 306. If the claim is written-off, the claim will then be in a status of closed 312 or outside collection 322. In other words, the claim may be written-off and the claim is closed. Or the claim may be written-off but may still be sent to an outside collection agency to collect the amount. As will be described in further detail below, methods, systems, and apparatuses disclosed herein automate the claim workflow, such that each claim is analyzed and a current status and a reason for the current status of the claim is automatically determined and a task that needs to be completed on the claim and an administrator responsible for handling the task is automatically identified. In some embodiments, the claim is automatically forwarded to the administrator member who is responsible for handling the task. Upon completion of the task, methods, systems, and apparatuses disclosed herein automate further processing of the claim by updating the claim and routing the claim to next corresponding step in the billing process. Therefore, for example, each of the arrows and/or steps illustrated in FIG. 3 can be done automatically, e.g., without any human intervention, by routing the claim based on its associated status code, reason code, and/or role. Routing in this manner from node to node as shown in FIG. 3 may be done without any human intervention in some embodiments, for example without any manual or decisional intervention into the routing process, because the processor determines how to route each claim based on its status code, reason code, and/or role.

In certain embodiments, claim related data may be imported and subsequently updated as the claim is routed through a series of steps automatically and without human intervention based on the status code, reason code and/or role code associated with the claim. After being routed and/or processed through one or more of the series of steps, the claim is transformed to an updated claim having an updated status code, reason code, and/or routing destination associated therewith. For example, a claim may change from a claim that needs verification to a claim that is ready to be submitted or is ready for payment based on one or more automated decisions made with respect to that claim. A billing automation system or platform may in include instructions that, when executed by a processor, cause the processor to receive an emergency medical claim, determine a status code corresponding to a current status of the claim and a reason code corresponding to a reason for the current status of the claim, identify, based on the status code and the reason code, a task that needs to be completed on the claim and/or an administrator associated with the task, and automatically and without human intervention, send the claim for payment, determine an expected payment, compare a received payment with the determined payment, and based on the comparison, determine or create an updated status code, reason code, and/or routing destination for the claim or associated with the claim. One or more of the above described steps, may be performed by hardware components, such as a processor, and/or may be embodied in machine-executable instructions, and/or performed automatically and/or without human intervention.

In certain embodiments, a master payer database may be provided, which includes payer fee schedules and other payer information to ensure accurate and efficient claim processing and payment. For example, once a claim is imported for processing, a payer fee schedule may be automatically applied to the claim and an expected payment determined based on the fee schedule before the claim is sent for payment. Payer claim mailing locations and fee schedules may be automatically updated to the database and automatically applied to claims, where the information may be tailored based on the state, city and/or zip code of the patient and/or the where the medical event took place.

In certain embodiments described herein, the claim may relate to one or more medical events, treatments or procedures performed. For example, the claim may be a claim for treatment provided to a patient in transit, on the move, or during transportation from one location to another location, e.g., in an emergency medical vehicle or a patient wearing a wearable defibrillator.

As another example, a claim may be in current status of denied 324 and the reason for the current status is "Full Denial." According to table 2, the role associated with "Denied" and "Full Denial" is "Denials." The claim may be forwarded to an administrator (e.g. a collector administrator or billing administrator) who is responsible for handling denied claims for rebilling. The administrator may complete the task of rebilling. The claim may then be updated with a status of ready for submission and be routed to node 306 for further processing. As another example, a claim may be in current status of denied 324 and the reason for the current status is "Denial Upheld." According to table 2, the role associated with "Denied" and "Denial Upheld" is "Appeals." The claim may be forwarded to an administrator member who is responsible for handling claim appeals. The administrator may complete the task of appeals. The claim may then be updated with a status of "Appealed" and be routed to node 326 for further processing.

Figure 4:
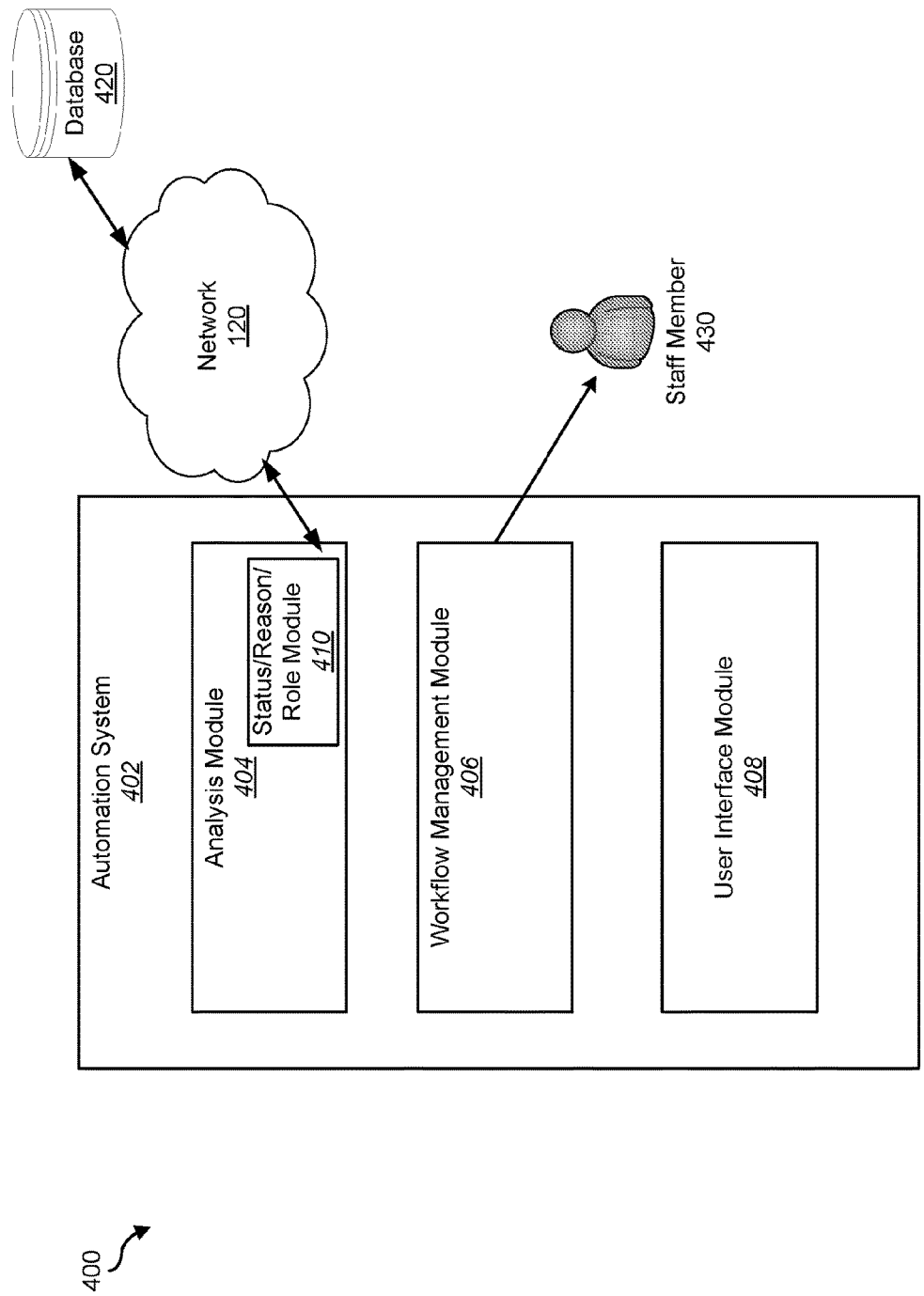
FIG. 4 illustrates a block diagram illustrating an automation system in accordance with an embodiment of the present disclosure.

FIG. 4 illustrates a block diagram illustrating an automation system in accordance with an embodiment of the present disclosure. Automation system 402 may reside on a client, such as an end-user device, and/or a server, such as a web server. One or more portions of automation system 402 may reside on different computers. One or more portions of the automation system 402 may reside at a network centric location. According to some embodiments, analysis and approval of resource references including automation system 402 may be implemented as part of a cloud computing environment. For example, automation system 402 may be distributed to various clients and servers through a cloud computer environment. As another example, automation system 402 may be updated at the network centric location and then distributed to various clients and servers. According to some embodiments and FIG. 2, automation system 402 may be resident in main memory 204.

In some embodiments, automation system 402 may include analysis module 404, workflow management module 406, and user interface module 408. Analysis module 404 may include status/reason/role module 410. Analysis module 404 may analyze a claim. In some embodiments, analysis module 404 may analyze the content of the claim for completeness and accuracy.

For example, analysis module 404 may determine if required information, such as patient information, physician authorization, submitter's signature, etc. is present on the claim. In some embodiments, analysis module 404 may query additional data for the claim. For example, analysis module 404 may query patient information to populate the claim. Analysis module 404 may obtain patient name, birth date, etc. based on patient social security number. Analysis module 404 may determine if information is correct. For example, analysis module 404 may determine if the billing amount is correct. In some embodiments, the analysis module 404 may determine or check the accuracy of the billing amount based on past occurrence and payment history of the payer for same or similar type claims. As described above, the billing amount for claim may be X dollar amount if the payer has paid same type of claim with X dollar amount in the past. If past occurrence and/or payment history of same type claim for the payer is not available, analysis module 404 may determine the billing amount based on past occurrence and/or payment history of similar type claims. In some embodiments, analysis module 404 may determine the billing amount in view of various factors, including, but not limited to, patient eligibility, patient co-payment, patient deductible, or patient co-insurance, more than one payer besides patient responsible for the claims. In some embodiments, analysis module 404 may determine a collection risk of the amount to be collected. Based on the determined collection risk, analysis module 404 may adjust the billing amount, for example, with a discount (e.g., 90% of the original billing amount).

Analysis module 404 may determine a status of a claim and a reason for the current status of the claim. In some embodiments, such determination may be based on examining the content of the claim. For example, analysis module may examine the content of the claim and determine that both primary and secondary authorization are required but missing. Accordingly, analysis module 404 may determine the current status of the claim to be "suspend bill" and a reason for the current status to be "primary authorization needed." In other embodiments, such determination may be based on the processing history of the claim, rather than the content of the claim. For example, from the processing history, the claim was in "suspend bill" status because both primary and secondary authorization were missing and primary authorization has been obtained, analysis module 404 may determine that the current status of the claim is "suspend bill" and the reason of the status for the bill is "secondary authorization needed."

Based on the current status of the claim and the reason for the current status of the claim, analysis module 404 may determine a role of the claim. In some embodiments, the reason indicates a task to be completed on the claim. The role identifies a function of administrator member or department who is responsible for handling the task. For example, based on "suspend bill" status and "primary authorization needed" reason, the role "authorizations" is determined. The role "authorizations" indicates the function of administrator member or department who is responsible for handling the task. The claim will be forwarded to the authorization group.

In some embodiments, the role of the claim is determined from a data source. Analysis module 404 may include a status/reason/role module 410. Status/reason/role module 410 may be communicably coupled to a data source 420. Data source 420 may store the triplet status/reason/role relations. In other words, status/reason/role module 410 may lookup role based on status and reason via data source 420. Data source 420 may be, but not limited to, a file (e.g. an excel spreadsheet with status/reason/role columns), or a database. In some implementations, data source 420 may be coupled to status/reason/role module 410 via network 120.

Still referring to FIG. 4, workflow management module 406 may manage the workflow of a claim. For example, workflow management module 406 may identify a responsible administrator that corresponds to a role of the claim. Using the same example as described above, for the role "authorizations," workflow management module 406 may identify an administrator responsible for claim authorization. Workflow management module 406 may identify the responsible administrator based on human resource information, such as an organizational chart. For example, based on the organizational chart, workflow management module 406 may identify head of the authorization group/department. Workflow management module 406 may also determine the responsible administrator based on other information such as leave, backup, etc. For example, workflow management module 406 may look into the calendar of the head of the authorization group and notice that the head is on vacation for a time period. During the time period that the group head is not available, workflow management module 406 may identify deputy head or a backup of the head of authorization group to be responsible administrator for role "authorizations." As will be described in further detail in relation to user interface module 408, the responsible administrator is configurable and may include any person or persons or administrators. In other words, a user may define who is responsible for a role of a claim. Workflow management module 406 may forward the claim to responsible administrator (e.g., administrator 430), via for example, emails. Workflow management module 406 may alert the responsible administrator if the task associated with the claim has not been completed after a certain time period. Upon completion of the task of the claim, workflow management module 406 may route the claim back into automation system 402 so that the claim may be processed further. In some embodiments, workflow management module 406 may communicate with analysis module 404, and analysis module 404 may continue to process the claim further (e.g., determine status/reason/role and forward to administrator responsible for next step). In some embodiments, workflow management module 406 may track claims in automation system 402 and provide reports and/or data regarding performance (e.g., average processing time, performance bottleneck or obstacle to paying the claim). In some embodiments, the processor of automation system 402 can perform the task associated with the role code, for example by sending a notification, and/or checking a status electronically. In other embodiments, the processor of automation system 402 confirms that the task associated with the role code has been undertaken and/or completed.

With continued reference to FIG. 4, automation system 402 may be customizable. In other words, a user can define workflow (e.g., status, reason, and role) and responsible administrator for a role of a claim. User interface module 408 may allow user to configure automation system 402. For example, a user may customize the workflow of the claim process. In some embodiments, the statuses, reasons, and/or roles associated with a claim are customizable. For example, the status/reason/role table (e.g., table 1, table 2) can be customized. Also, each node (or a processor, whether central or at each node) can update one or more of the codes associated with the claim based on changed circumstances or position within the workflow.

For example, user interface module 408 may present an interface with blocks and arrows (e.g., FIG. 3) such that user may define a sequence of the steps. For example, in relation to FIG. 3, a user may customize Follow-up 320 such that if there is a payment discrepancy, with $0 paid write-off, the claim only goes to Outside Collection 322. In other words, the claim does not follow the path/arrow between Follow-up 320 and Closed 312.

As another example, a user may configure responsible administrator for a role by mapping the role with responsible administrator information (e.g., name, email address) etc. Automation system 402 may adapt to large or small organizations with various numbers of administrators for claim processing. For example, user may customize via user interface module 408 such that multiple status/reason/role are handled by one person, or one status/reason/role is handled by multiple administrator members, each of who handles a subset of claims depending on the services associated with the claims. In other words, granularity of claim processing may be adjusted.

Figure 5:
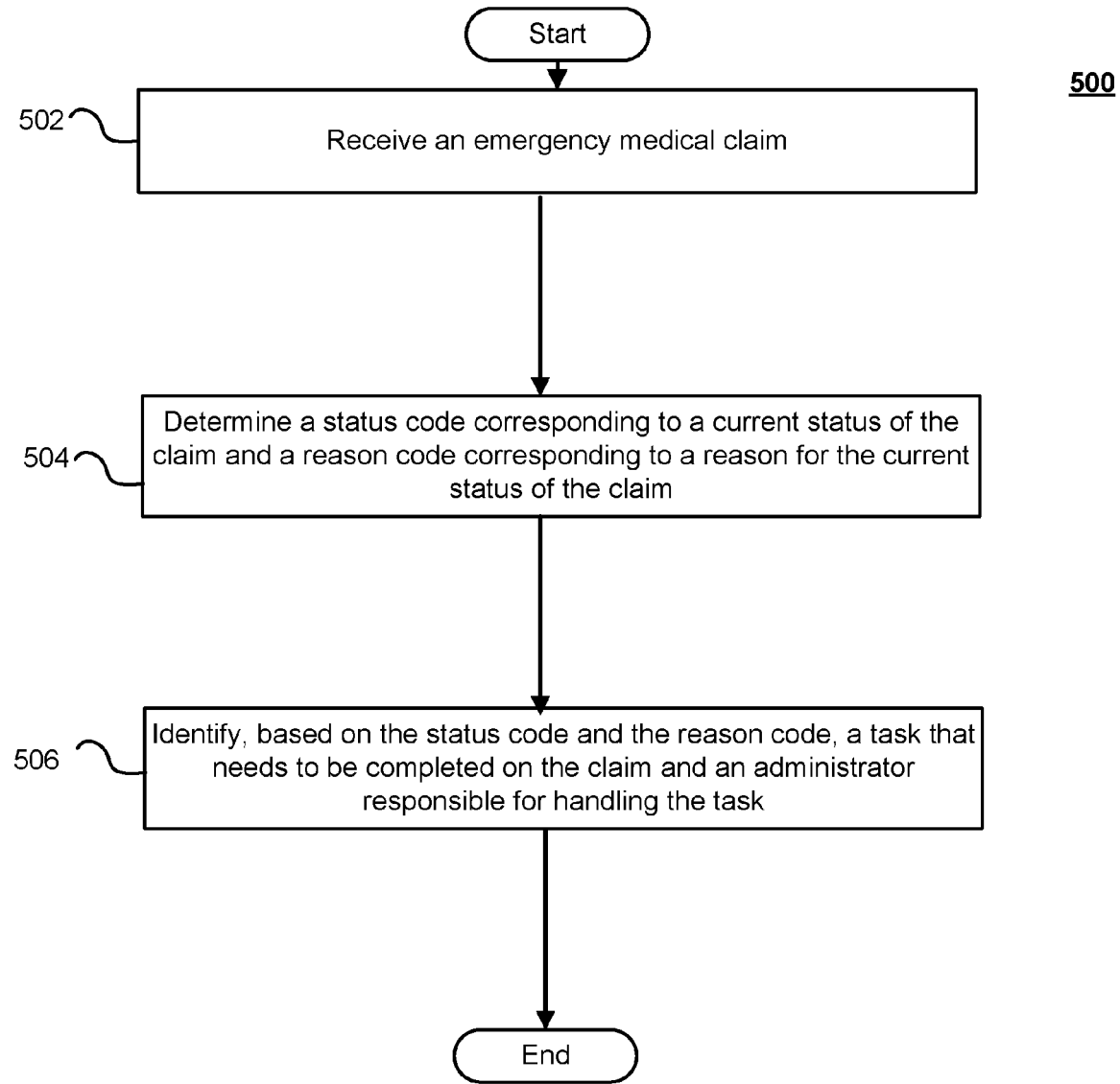
FIG. 5 shows a flowchart for the automation system in accordance with an example method of the present disclosure.

FIG. 5 shows a flowchart for the automation system in accordance with an example method of the present disclosure. Process 500 may include: receiving an emergency medical claim (e.g. a claim for billing or reimbursement for service rendered, for example emergency medical services) (block 502); determining a current status of the claim and a reason for the current status of the claim (block 504); and identifying, based on the current status and the reason, a task that needs to be completed on the claim and an administrator responsible for handling the task (block 506).

Process 500 may include receiving an emergency medical claim (block 502). In some implementations, the emergency medical claim may be imported from a service order. In some embodiments, the emergency medical claim may be associated with medical services that have been rendered. In some embodiments, the emergency medical claim may be associated with medical services that need pre-authorization. In certain embodiments, the emergency medical claim may be a claim for treatment provided to a patient in transit or during transportation from one location to another location or in a mobile environment, e.g., in an emergency medical vehicle or a patient wearing a wearable defibrillator.

Process 500 may include determining a current status of the claim and a reason for the current status of the claim (block 504). As described above, in some embodiments, the current status and the reason may be determined based on the content of the claim. In some embodiments, the current status and the reason may be determined based on processing history of the claim. The current status may include, but is not limited to, the status 302 to 326 described in relation to FIG. 3. The reason may include, but is not limited to, clinical documentation needed, authorization needed, patient complaint, insurance verification needed.

Process 500 may include identifying, based on the current status and the reason, a task that needs to be completed on the claim and an administrator responsible for handling the task (block 506). As described above, in some embodiments, a role may identify a function of administrator member or department who is responsible for handling the task. The role may then be mapped to at least one administrator or department that is responsible for handling the task for the claim. For example, based on the current status "follow up" and the reason "no response from payer," the role "payer follow-up" may be determined. Based on the role "payer follow-up," an administrator who is responsible for "payer follow-up" may be identified.

Process 500 may be modified by removing, adding, or rearranging any of the aforementioned stages. For example, process 500 may be modified by adding an additional stage of forwarding the claim to the administrator responsible for handling the task. The claim may be forwarded to the responsible administrator. In some embodiments, the automation system 402 includes a user interface within an application, for example a web-based or cloud-based application, which includes a claims inbox, and when the claim is routed to a particular administrator that is associated with a user, the user sees the claim appear or populate or link on the user's inbox page of the application. When the user completes the user's tasks, the status and/or reason codes change, which causes the claim to be further routed and/or reassigned to a different administrator whose role matches the role code of the claim's new status and reason code combination, according to some embodiments. In other embodiments, claims or links thereto may be forwarded via email or other messaging process to the administrator associated with the role code or the task. In some embodiments, the responsible administrator may be notified that a new task has arrived. In some embodiments, the administrator may be a head (department head, or group leader) of administrator members responsible for the task. The head may assign the task to other administrator members. Upon the completion of the task, the claim is automatically put back in the processing procedure. For example, an administrator member may complete "authorization" and click on the "complete" button, and the claim may be further processed (e.g., next step in the process). In some embodiments, the workflow and/or responsible administrator are configurable (e.g., customizable). Such configuration may be achieved via a user interface.

Figure 6:
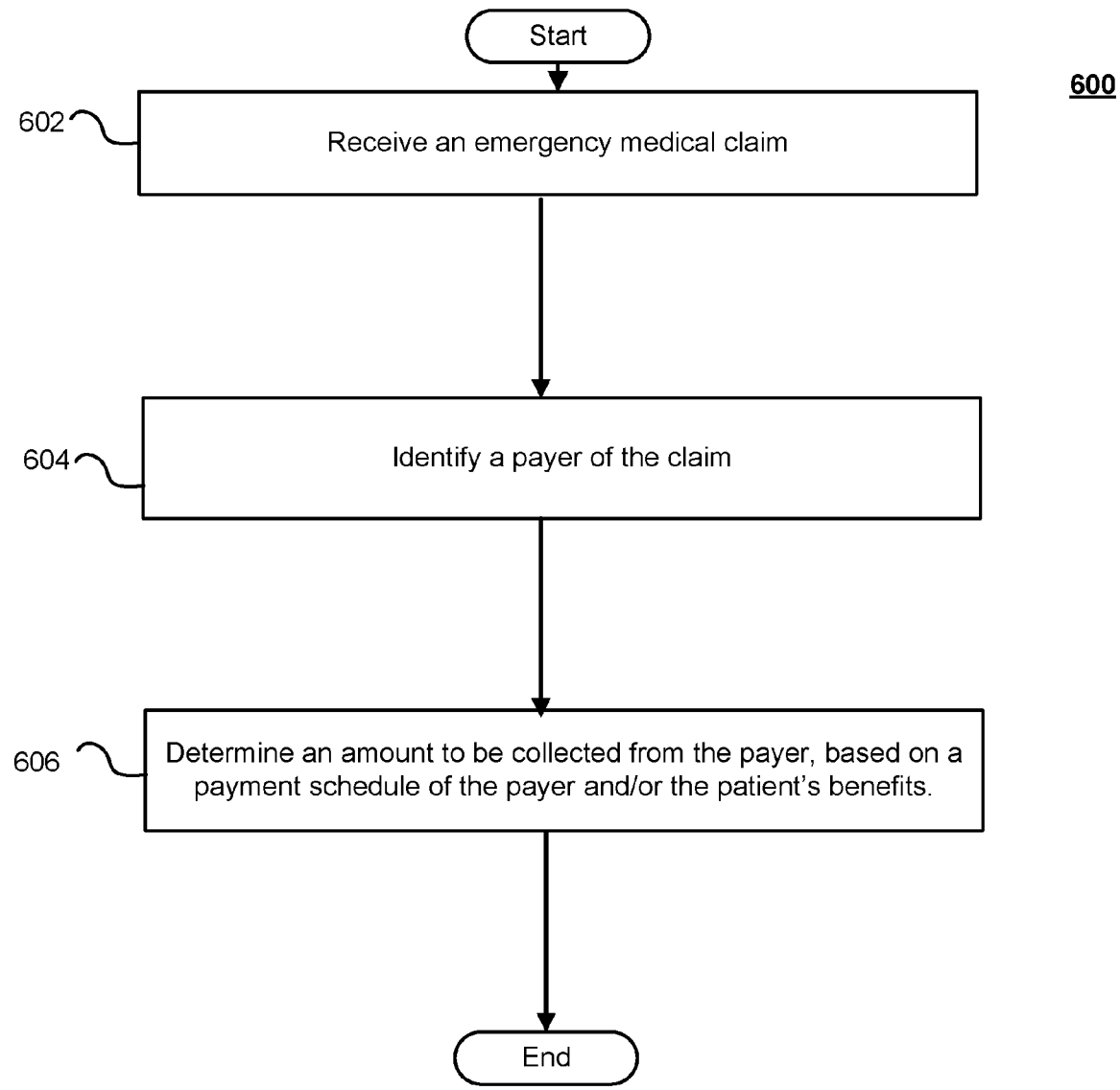
FIG. 6 shows a flowchart for the automation system in determining a billing amount, in accordance with an example method of the present disclosure.

FIG. 6 shows a flowchart for the automation system in determining a billing amount, in accordance with an example method of the present disclosure. Process 600 may include: receiving an emergency medical claim (block 602); identifying a payer of the claim, e.g., based on information regarding the health insurance of the patient who is the subject of the claim (block 604); and determining an amount to be collected from the payer, based on a past payment of the payer for at least one of a same type claim or a similar type claim (block 606). In some embodiments, the amount to be collected may be adjusted if there are more than one payer (besides the patient) responsible for the claim. In some embodiments, the amount to be collected from the payer may be adjusted based on patient eligibility, patient co-payment, patient deductible, and/or patient co-insurance.

Process 600 may be modified by removing, adding, or rearranging any of the aforementioned stages. For example, process 600 may be modified by removing the block related to determining an amount to be collected from the payer, based on a past payment of the payer for at least one of a same type claim or a similar type claim (block 606), and adding a step of determining an amount to be collected from the payer, based on a fee schedule of the payer and the patient's benefits (which may be governed by a fee schedule of a third party other than the payer), according to some embodiments. As described above, a payer may associate its fee schedule to a third party. In some embodiments, the third party is Medicare or Medicaid. In some embodiments, the payer may pay a percentage (e.g., 90% or 110%) of the third party fee schedule. Accordingly, the amount to be collected may be determined based on a third party fee schedule. In some embodiments, a payer's fee schedule may be updated automatically and without human intervention, e.g., in accordance with a third party fee schedule update. In other words, if a third party updates its schedule (e.g., annual update of Medicare or Medicaid fee schedule), the payer fee schedule will be updated accordingly.

In certain embodiments, a system for automatically processing emergency medical claims may include a payer plan database that stores payer plan information. The system may also include one or more processors and a memory. The memory includes instructions that when executed by the processor, causes the processor to perform one or more of the following steps: receive an emergency medical claim; identify a payer of the claim, e.g., based on information provided in the claim, based on information from the payer plan database and/or based on information regarding the health insurance of the patient who is the subject of the claim; determine an expected claim payment amount to be collected from the payer, e.g., based on one or more medical services that are the subject of the claim; and adjust the expected claim payment amount based on at least one of a payment schedule of the payer, a past payment of the payer for a same or similar type of claim, patient eligibility, patient co-payment, patient deductible, patient co-insurance, and/or a determined collection risk. The system may also receive a payment posted amount from the payer and compare the payment posted amount to the expected claim payment amount. The claim may be adjusted if the payment posted amount has been posted with a payment discrepancy between the payment posted amount and an expected claim payment amount. The adjusted claim may then be output on a display or routed for further processing, investigation or analysis regarding the discrepancy. One or more of the above described steps, may be performed by hardware components, such as a processor, and/or may be embodied in machine-executable instructions, and/or performed automatically and/or without human intervention.

As illustrated in FIGS. 3, 5, and 6, and described above, once the claim is ready for submission, the claim may be submitted to the payer for payment; in other words, a bill associated with the claim may be submitted. This may be a mailing and/or an electronic communication, or, in some cases, a debit request with a financial institution, according to some embodiments.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for automatically processing a medical claim, the system comprising:
one or more servers configured to implement a billing automation platform;
a navigation device associated with a patient transport vehicle and comprising a global positioning system (GPS), the navigation device configured to collect patient transport information comprising a location of a medical encounter; and
a computing device communicably coupled to the navigation device and to the one or more servers, the computing device configured to
receive the patient transport information from the navigation device,
receive patient charting information for the medical encounter, and
transmit the patient transport information with the patient charting information to the one or more servers,
wherein the billing automation platform is configured to
receive the patient transport information with the patient charting information,
access at least one fee schedule based on the location of the medical encounter,
automatically populate the medical claim for the medical encounter based on the patient charting information, the patient transport information, and the at least one fee schedule, and
automatically route the medical claim through a plurality of workflow paths of an automated claim processing workflow, wherein routing the medical claim comprises
(a) associating the medical claim with first routing information comprising a first status code and a first reason code of a plurality of status codes and a plurality of reason codes based at least in part on the medical claim,
(b) directing the medical claim through a first workflow path of the plurality of workflow paths based on the first routing information, wherein the directing results in the first routing information being updated to a next routing information comprising a next status code and a next reason code of the plurality of status codes and reason codes, (c) directing the medical claim through a next workflow path of the plurality of workflow paths based on the next routing information, and (d) repeating step (c) for the plurality of workflow paths.

2. The system of claim 1, wherein the patient charting information comprises an electronic patient care record (ePCR).

3. The system of claim 2, wherein the computing device comprises a mobile device.

4. The system of claim 3, wherein the mobile device comprises a smartphone or a tablet.

5. The system of claim 3, wherein the mobile device comprises at least one of a touch screen or voice recognition data entry.

6. The system of claim 3, wherein the mobile device is communicably coupled to a patient monitor and/or defibrillator.

7. The system of claim 1, wherein the billing automation platform is configured to automatically update one or more fee schedules of the at least one fee schedule based on a third-party fee schedule update.

8. The system of claim 7, wherein the third-party fee schedule update is a Medicare or a Medicaid fee schedule update.

9. The system of claim 1, wherein the billing automation platform is configured to determine an expected claim payment amount for the medical claim.

10. The system of claim 9, wherein the billing automation platform is configured to access a plurality of claim payment information comprising at least one of patient health insurance information, patient co-insurance information, patient deductible information, or patient eligibility information.

11. The system of claim 9, wherein the billing automation platform is configured to determine the expected claim payment amount for the medical claim based on a payment history of a payer for a same type of medical claim or a similar type of medical claim.

12. The system of claim 9, wherein the billing automation platform is configured to determine the expected claim payment amount based on a determined collection risk for the medical claim.

13. The system of claim 1, wherein the billing automation platform is configured to verify first demographic information.

14. The system of claim 13, wherein the billing automation platform is configured to query for additional patient demographic information based on the first demographic information.

15. The system of claim 1, wherein the billing automation platform is configured to analyze content of the medical claim for completeness and accuracy.

16. The system of claim 1, wherein each status code of the plurality of status codes corresponds to two or more reason codes of the plurality of reason codes.

17. The system of claim 1, wherein each status code of the plurality of status codes and each reason code of the plurality of reason codes corresponds to a respective role or a plurality of roles.

18. The system of claim 1, wherein the one or more servers configured to implement the billing automation platform are configured to communicably couple to one or more dispatch servers.

19. The system of claim 18, wherein the one or more servers configured to implement the billing automation platform are configured to communicably couple to the one or more dispatch servers to access emergency dispatch information.

20. The system of claim 1, wherein the one or more servers are configured to implement the billing automation platform as part of a cloud computing environment.

21. The system of claim 1, wherein the billing automation platform is configured to identify pre-authorization requirements.

22. The system of claim 1, wherein the billing automation platform is configured to determine medical claim payment information based on a geographic location of a patient.

* * * * *